(12) United States Patent
Saito

(10) Patent No.: US 9,144,380 B2
(45) Date of Patent: Sep. 29, 2015

(54) ADAPTIVE OPTICAL APPARATUS, IMAGE OBTAINING APPARATUS, METHOD FOR CONTROLLING ADAPTIVE OPTICAL APPARATUS, AND STORAGE MEDIUM

(71) Applicant: CANON KABUSHIKI KAISHA, Tokyo (JP)

(72) Inventor: Kenichi Saito, Pittsford, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 19 days.

(21) Appl. No.: 14/096,298

(22) Filed: Dec. 4, 2013

(65) Prior Publication Data

US 2014/0160435 A1 Jun. 12, 2014

(30) Foreign Application Priority Data

Dec. 10, 2012 (JP) ................. 2012-269787

(51) Int. Cl.
*A61B 3/10* (2006.01)
*A61B 3/00* (2006.01)
*A61B 3/14* (2006.01)

(52) U.S. Cl.
CPC ........................................ *A61B 3/14* (2013.01)

(58) Field of Classification Search
USPC ............................................... 351/200–246
See application file for complete search history.

(56) References Cited

U.S. PATENT DOCUMENTS

| 6,890,076 B2 | 5/2005 | Roorda |
| 8,506,082 B2 | 8/2013 | Saito |
| 8,699,015 B2 | 4/2014 | Saito et al. |
| 2003/0053026 A1 | 3/2003 | Roorda |
| 2003/0174281 A1 | 9/2003 | Herekar et al. |
| 2004/0061830 A1 | 4/2004 | Hellmuth et al. |
| 2007/0291230 A1 | 12/2007 | Yamaguchi et al. |
| 2011/0242487 A1 | 10/2011 | Yuasa et al. |
| 2012/0274904 A1 | 11/2012 | Saito et al. |
| 2013/0021576 A1 | 1/2013 | Saito |
| 2013/0208243 A1* | 8/2013 | Sakagawa ..................... 351/211 |
| 2014/0055748 A1 | 2/2014 | Saito |

FOREIGN PATENT DOCUMENTS

| JP | 2005-501587 A | 1/2005 |
| JP | 4157839 B2 | 10/2008 |
| WO | 03/020121 A1 | 3/2003 |

* cited by examiner

*Primary Examiner* — Mohammed Hasan
(74) *Attorney, Agent, or Firm* — Fitzpatrick, Cella, Harper & Scinto

(57) ABSTRACT

An adaptive optical apparatus comprising: a shielding unit configured to shield diffracted light that is generated at an aberration correction unit that is irradiated with returning light, wherein the returning light returns from an object to be examined that is irradiated with light; a detection unit configured to detect an aberration of the returning light through an aperture of the shielding unit; and a control unit configured to control the aberration correction unit based on a detection result of the detection unit.

20 Claims, 3 Drawing Sheets

ADAPTIVE OPTICAL APPARATUS, IMAGE OBTAINING APPARATUS, METHOD FOR CONTROLLING ADAPTIVE OPTICAL APPARATUS, AND STORAGE MEDIUM

BACKGROUND OF THE INVENTION

1. Field of the Invention

The present invention relates to an adaptive optical apparatus, an image obtaining apparatus, a method for controlling the adaptive optical apparatus, and a storage medium, and particularly relates to a technology for correcting aberrations generated by an object to be examined.

2. Description of the Related Art

In recent years, the technology of adaptive optics (AO) that corrects even higher-order wavefront aberrations using an active optical element has been put to practical use and applied in various fields. This technology successively measures wavefront aberrations of probe light or signal light, which may be generated due to the characteristics of a measurement target itself, variations in a measurement environment, and the like, using a wavefront sensor and corrects the wavefront aberrations using a wavefront corrector such as a deformable mirror (hereinafter referred to as "DM"), a spatial light modulator (hereinafter referred to as "SLM"), or the like, and is receiving attention especially in the field of systems for examination of the eye's retina.

As examples of such ophthalmic devices, in addition to a fundus camera, an SLO (Scanning Laser Ophthalmoscope) that obtains a two-dimensional image of the retina and an OCT (Optical Coherence Tomography) that obtains a tomographic image of the retina are known. The SLO and the OCT scan a light beam one- or two-dimensionally on the retina using a scanning unit, receive reflected and backscattered light from the retina, and obtain a two-dimensional image or a three-dimensional image of the retina.

Japanese Patent No. 4157839 discloses an SLO in which while a scanning unit two-dimensionally scans light from a light source on a retina, a wavefront detector receives a part of returning light reflected from the retina and detects a wavefront, an aberration corrector corrects the wavefront of light irradiated onto an eye to be examined and the wavefront of the returning light, and a part of the returning light is received to form an image.

Here, generally, a DM of a type having a configuration in which a plurality of micromirrors are periodically and two-dimensionally arrayed or a liquid crystal type SLM in which a plurality of micropixels are periodically arrayed in a two-dimensional matrix is used as the aberration corrector that corrects the wavefront aberrations. Since these aberration correctors have a structure in which gaps are periodically distributed among the plurality of pixels, diffracted light will be generated when the aberration corrector is irradiated with light. If the wavefront detector is irradiated with the diffracted light, precise wavefront detection may be affected, resulting in a decrease in the accuracy of aberration correction, and thus there is a possibility that the image quality of the obtained image may also decrease.

SUMMARY OF THE INVENTION

The present invention has been made in consideration of the above-described problems, and provides a technology for reducing an effect that is exerted on wavefront detection by diffracted light that is generated when an aberration corrector is irradiated with light.

According to one aspect of the present invention, there is provided an adaptive optical apparatus comprising: a shielding unit configured to shield diffracted light that is generated at an aberration correction unit that is irradiated with returning light, wherein the returning light returns from an object to be examined that is irradiated with light; a detection unit configured to detect an aberration of the returning light through an aperture of the shielding unit; and a control unit configured to control the aberration correction unit based on a detection result of the detection unit.

Further features of the present invention will be apparent from the following description of exemplary embodiments with reference to the attached drawings.

DESCRIPTION OF THE EMBODIMENTS

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Shielding Unit Shielding Diffracted Light Generated at Aberration Correction Unit An SLO (Scanning Laser Ophthalmoscope) and an OCT (Optical Coherence Tomography) scan a light beam one- or two-dimensionally on a retina using a deflector and synchronously measure reflected and backscattered light from the retina, thereby obtaining a two-dimensional image or a three-dimensional image of the retina.

The spatial resolution (hereinafter referred to as "lateral resolution") of the obtained image in a surface direction (lateral direction) of the retina essentially depends on the spot diameter of a beam that is scanned on the retina. To reduce the spot diameter of the beam focused on the retina, the diameter of the beam incident on the eye can be increased. However, the imperfect uniformity of the curved surface shape and the refractive index of the cornea and the crystalline lens, which take major roles in refraction in the eyeball, causes higher-order aberrations in the wavefronts of light passing through them. Therefore, even if a wide beam is incident on the eye, the beam cannot be focused to a desired spot diameter on the retina but rather diverges. As a result, the lateral resolution of the obtained image decreases, and in the case of a confocal optical system, the S/N of the obtained image signal will also decrease. Thus, conventionally, a common approach was to direct a narrow beam of about 1 mm, which is less likely to be affected by aberrations of the eye's optical system, into the eye and form a spot of about 20 μm on the retina.

In contrast, in these years, the technology of adaptive optics is becoming introduced. With this technology, even in the case where a wide beam of about 7.5 mm is incident on the eyeball, it is possible to focus the beam to as small as less than 2 μm, which is close to the diffraction limit, on the retina by means of wavefront compensation and to obtain a high-resolution SLO image or OCT image.

Configuration of Adaptive Optical Apparatus

Figure 1:
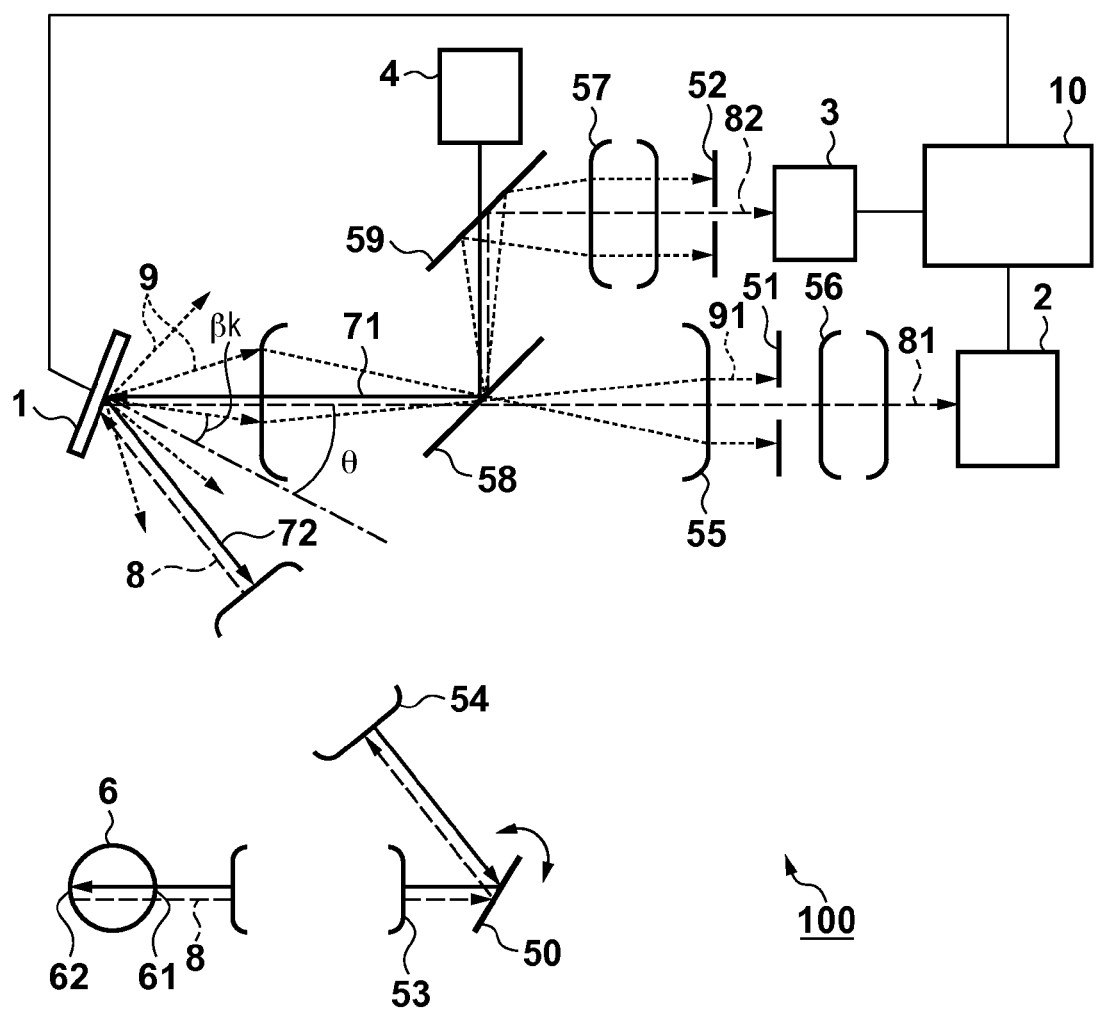
FIG. 1 is a diagram showing an example of the configuration of an adaptive optical apparatus according to a first embodiment.

FIG. 1 shows an example of the configuration of an adaptive optical apparatus 100 according to a first embodiment. It should be noted that an SLO that has an adaptive optics function will also be referred to as an AO-SLO. A light source 4, which functions as an irradiation unit, emits light 71 having a wavelength λ (840 nm). A part of the light 71 is transmitted through a beam splitter (BS) 59, and a part of the transmitted light 71 is reflected by a beam splitter (BS) 58. The reflected light 71 passes through a part of an optical system 55 and is irradiated onto a reflective liquid crystal SLM 1, which is an example of an aberration correction unit, as irradiation light at an incident angle θ and reflected by the reflective liquid crystal SLM 1 as reflected light. Then, the reflected light passes through an optical system 54 and is deflected and reflected by a deflector 50, which is an example of a scanning unit, such as a galvanometer mirror or a polygon mirror. It should be noted that the incident angle θ refers to an angle of the irradiation light with respect to a line normal to a reflecting surface of the reflective liquid crystal SLM 1 (alternate long and short dash line in FIG. 4). In addition, the light from the deflector 50 passes through an optical system 53, is incident on an eye to be examined 6, which is an example of an object to be examined, and is scanned on a retina 62. Here, the light that illuminates the eye to be examined is indicated by solid arrows.

It should be noted that in addition to the eye to be examined, for example, a specimen of the skin or the like is conceivable as an example of the object to be examined. Also, the adaptive optical apparatus according to this embodiment is applicable not only to ophthalmic apparatuses but also to, for example, an endoscope. Moreover, the aberration correction unit may be an SLM or may be a DM. The SLM may be of reflection type or may be of transmission type, and there is no limitation to a liquid crystal type. Any device having a structure in which gaps are periodically distributed among a plurality of pixels and having a configuration in which diffracted light is generated when the wavefront corrector is irradiated with light may be used as the aberration correction unit. Examples thereof include a DM of a type composed of a plurality of micromirrors that are periodically and two-dimensionally arrayed and a liquid crystal SLM in which a plurality of micropixels are periodically arrayed in a two-dimensional matrix.

Here, the characteristics of DMs generally do not depend on the wavelength with respect to a wide range of wavelengths if the vapor-deposited film of the DMs is optimized, and thus DMs can be widely used. However, DMs have the following features: computation, such as setting of a quasi-inverse matrix that is necessary to calculate a correction value, is complicated; and DMs are extremely expensive. On the other hand, liquid crystal SLMs have the wavelength dispersion characteristics of the liquid crystal material and the dependence of diffraction efficiency on the wavelength, and furthermore, while one polarization component can be corrected, the other polarization component cannot be corrected. However, liquid crystal SLMs have the following features: liquid crystal SLMs are extremely inexpensive when compared with DMs; and control is easy because the measured wavefront aberration shape can be displayed as it is. It should be noted that in the case where aberration correction is performed using a liquid crystal SLM in real time during capturing of an image of the object to be examined, since the liquid crystal SLM has the dependence on the wavelength, it is preferable to set the wavelength of light for image capturing and the wavelength of light for aberration correction at the same wavelength. For example, it is conceivable to use a common light source as both the source of the light for image capturing and the source of the light for aberration correction. Naturally, when different liquid crystal SLMs are used for different wavelengths, the wavelengths of these two kinds of light may be set at mutually different wavelengths.

Returning light 8 diffusely reflected by the retina 62 propagates through the optical path of the light illuminating the eye to be examined in the opposite direction. Then, a part of the returning light 8 is transmitted along the BS 58 and, after passing through an aperture of a pinhole plate 51, irradiated onto a wavefront sensor 2, which is an example of a detection unit, via the optical system 56 as wavefront detection light 81. Another part of the returning light 8 is reflected by the BS 58, and then a part of the reflected returning light 8 is further reflected by the BS 59, passes through the optical system 57 and an aperture of a pinhole plate 52, and is irradiated onto a light detector 3, which functions as a measurement unit, as image signal light 82. Here, the returning light 8 from the eye to be examined is indicated by dashed arrows. The role of the pinhole plate 51 will be described later. In addition, the wavefront detection light 81 and the image signal light 82 will also be expressed as "returning light".

The wavefront sensor 2 may be a Shack-Hartmann sensor that is composed of a microlens array and a two-dimensional image sensor, and detects wavefront aberrations from the displacements of individual spots in the obtained Hartmann image and sends the detected wavefront aberrations to a computer 10, which is an example of a control unit. The light detector 3 may be a photodiode or a photomultiplier tube, and measures the image signal light 82 irradiated thereon, converts it into an electric signal, and sends the electric signal to the computer 10. This electric signal is synchronized with a synchronizing signal from the deflector 50, and so the computer 10, which functions as an image obtaining apparatus, forms two-dimensional image information.

At this time, with regard to the light 72 incident on the eye to be examined 6, the beam diameter of the light 72 when irradiated onto an anterior ocular segment 61 is set at 6 mm, and if the eye's optical system has no aberration, the light 72 is focused to about 3 μm on the retina 62. However, actually, the imperfection of the eye's optical system generates aberrations and forms a distorted spot on the retina 62. Also, the returning light 8 from the retina 62 suffers aberrations as well, and forms a spot that is similarly distorted and blurred on the pinhole plate 52, which is disposed in a position that is optically substantially conjugate to the retina 62. Thus, the signal strength detected by the light detector 3 is weak.

Here, based on detection result data of the wavefront aberrations detected by the wavefront sensor 2, the computer 10 forms and sends instruction value data for wavefront aberration correction to the reflective liquid crystal SLM 1. The reflective liquid crystal SLM 1 displays a correction screen on a liquid crystal panel in accordance with the instruction value data. Thus, the light 72 reflected by the reflective liquid crystal SLM 1 is given aberrations having a sign opposite to that of the aberrations of the eye's optical system. When this light 72 is incident on the eye to be examined 6, the wavefront aberrations are offset (corrected), and the light 72 is ideally focused on the retina 62 as a favorable spherical wave. Conversely, the diffusely reflected returning light 8 is given aberrations when emerging from the eye to be examined 6, but the returning light 8 is corrected by the reflective liquid crystal SLM 1, and after reflected by the reflective liquid crystal SLM 1, the returning light 8 propagates with a favorable wavefront and is ideally focused on the pinhole plate 52. Most of the focused returning light 8 passes through the aperture of the pinhole plate 52 and is detected by the light detector 3 as a strong image signal. In the above-described manner, the aberrations of the eye to be examined 6 are corrected by the adaptive optics function, so that a bright and high-resolution image is obtained.

Diffracted Light Generated when Aberration Correction Unit is Irradiated with Light At this time, since the reflective liquid crystal SLM 1 has a pixel periodic structure in which micropixels are periodically arrayed in a two-dimensional matrix structure, when the light 71 is irradiated onto and reflected by the reflective liquid crystal SLM 1, a plurality of diffracted light groups 9 are generated. Diffracted light may be generated at the liquid crystal SLM not only by the light emitted from the light source and incident on the eye to be examined (forward path) but also by the returning light (return path). However, diffracted light is mainly caused by the light emitted from the light source and incident on the eye to be examined (forward path), and the orders of magnitude are larger than those of the diffracted light that is generated at the liquid crystal SLM due to the returning light (return path). Here, rays of diffracted light are indicated by dotted arrows. The diffraction angle (angle from the direction of the normal to the plane of the reflective liquid crystal SLM 1) βn of each order has a relationship as given by equation (1) below:

$$\beta n = \sin^{-1}(n \cdot \lambda / P - \sin\theta) \quad (1)$$

where P is the pixel pitch of the reflective liquid crystal SLM 1, λ is the wavelength of the irradiation light, θ is the angle at which the irradiation light is incident on the reflective liquid crystal SLM 1, and n is an integer.

Figure 2:
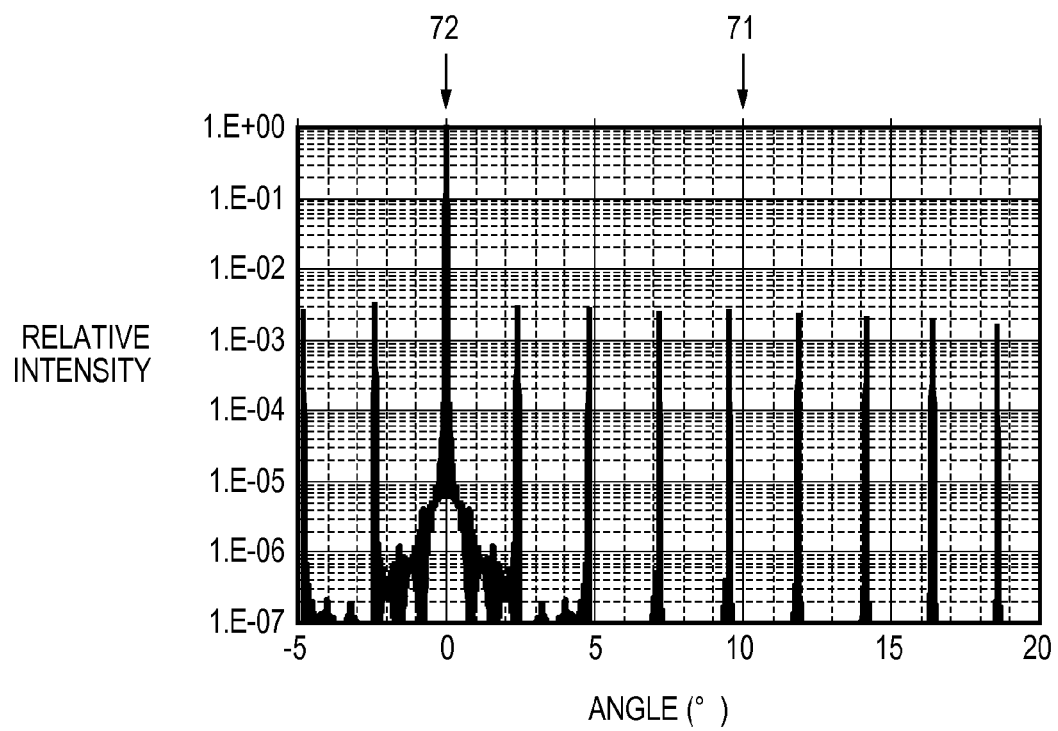
FIG. 2 is an explanatory diagram of characteristics of diffraction angles of diffracted light rays that are generated at a reflective liquid crystal SLM according to the first embodiment.

For example, when the wavelength λ is 840 nm, the pixel pitch P is 20 μm, and the incident angle θ is 5°, diffracted light rays are generated at angles as shown in FIG. 2. Here, FIG. 2 is a graph representing the characteristics of the diffraction angle of each diffracted light ray that is generated at the reflective liquid crystal SLM according to this embodiment. It should be noted that the angle on the horizontal axis is indicated by assuming that the reflection angle of the reflected light (zero-order diffracted light), which is the light 72, is 0°. Therefore, the angle of the light 71 is 10°. It should be noted that the wavelength λ of the light source and the pixel pitch P of the reflective liquid crystal SLM 1 determine the angle between diffracted light rays, and the incident angle θ determines the angles of diffracted light.

If the angle of one of the diffracted light rays is close to the angle of the irradiation light 71, that is, if a k-th order diffraction angle βk is close to −θ (in the example shown in FIG. 2, the angle of the fourth-order diffracted light is close to the angle of the irradiation light with a slight difference of about) 0.5°, some diffracted light rays of the plurality of diffracted light rays are incident on the wavefront sensor 2, and wavefront detection cannot be correctly performed. Moreover, if some diffracted light rays of the plurality of diffracted light rays are irradiated onto the light detector 3, a certain signal is constantly added, resulting in a low-contrast image.

Shielding Unit Shielding Diffracted Light Generated at Aberration Correction Unit To reduce the effect of diffracted light on wavefront detection, diffracted light that is generated when the aberration corrector is irradiated with light is shielded upstream of the wavefront detector.

First, the pinhole plate 51, which is an example of a shielding unit that shields the diffracted light, is disposed between the reflective liquid crystal SLM 1 and the wavefront sensor 2. The pinhole plate 51 has a pinhole, which is an example of an aperture, in order to allow the wavefront detection light 81 to pass through without being blocked. Moreover, for this purpose, it is preferable that the aperture of the pinhole plate 51 is provided in a position at which the wavefront detection light 81 is focused. Specifically, it is preferable that the pinhole plate 51 is disposed in a position that is optically substantially conjugate to the retina 62. Thus, the position at which the wavefront detection light 81 is irradiated onto the shielding unit and the position at which the diffracted light is irradiated onto the shielding unit can be spaced apart as far as possible.

Moreover, it is necessary to satisfy a condition that a diffracted light ray 91 of the order that is adjacent to the wavefront detection light 81, of a plurality of diffracted light rays, is not allowed to pass through the pinhole plate 51. Specifically, it is necessary that the aperture of the pinhole plate 51 has a length (size) that is shorter (smaller) than the distance between the position at which the diffracted light ray of the order that is adjacent to the wavefront detection light 81, of the plurality of diffracted light rays, is irradiated onto the pinhole plate 51 (position of the diffracted light at the shielding unit) and the position at which the wavefront detection light 81 is irradiated onto the pinhole plate 51 (position of the returning light at the shielding unit). For example, when the aperture of the pinhole plate 51 has a radius r, the distance d between these two positions on the plane of the pinhole plate 51 is required to satisfy expression (2) below:

$$|d| > r \quad (2).$$

Since the reflective liquid crystal SLM 1 is disposed in a position that is conjugate to the pupil (position that is optically substantially conjugate to the anterior ocular segment), and the pinhole plate 51 is disposed in a position that is conjugate to the image plane, the distance d is expressed as given by equation (3) below:

$$d = (\theta - \beta k) \cdot f \quad (3)$$

where f is the focal length of the optical system 55 between the reflective liquid crystal SLM 1 and the pinhole plate 51, and k is an integer.

From equations (1) and (3), expression (2) becomes expression (4) below:

$$|\{\theta - \sin^{-1}(k \cdot \lambda / P - \sin\theta)\} \cdot f| > r \quad (4)$$

For given λ, P, f, and r, if the incident angle θ, at which light is incident on the reflective liquid crystal SLM 1, is set so as to satisfy the condition of expression (4), the diffracted light is blocked by the pinhole plate 51 and is no longer irradiated onto the wavefront sensor 2, so that a favorable Hartmann image that is free from unwanted light is obtained. This enables accurate and stable wavefront detection. It should be noted that if the left-hand side of expression (4) is zero, the diffracted light and the returning light are at an equal angle, and this means that the wavefront sensor 2 is irradiated with the diffracted light irrespective of the size of the pinhole.

For example, if the focal length f of the optical system 55 is −80 mm, and the radius r of the aperture of the pinhole plate

Figure 3:
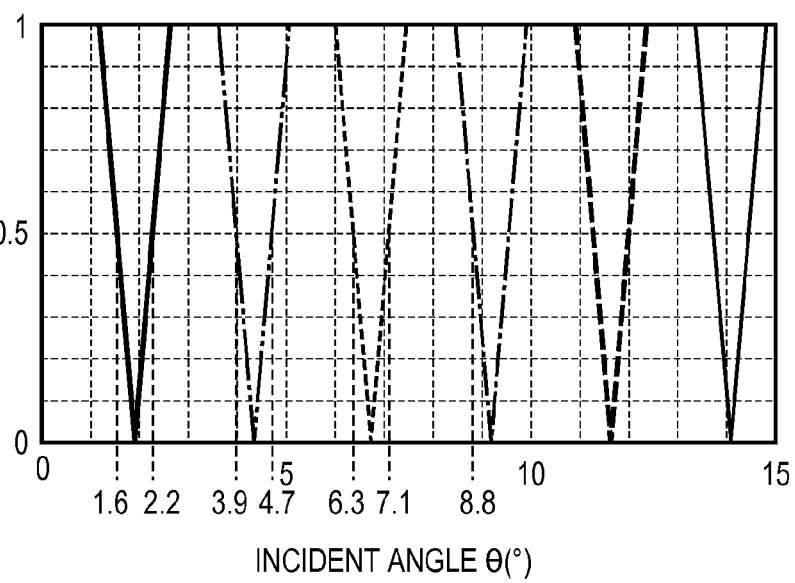
FIG. 3 is an explanatory diagram of the conditions for an optimal incident angle according to the first embodiment.

51 is 0.5 mm, the incident angle θ of the light 71 can be set to a range (0° to about 1.6°, about 2.2° to about 3.9°, about 4.7° to about 6.3°, about 7.1° to about 8.8°, . . . ) in which the position d of the diffracted light exceeds 0.5 mm in the graph shown in FIG. 3.

It should be noted that it also is required that the light detector 3 for obtaining images is not irradiated with the diffracted light. Here, the aperture of the pinhole plate 52 for forming a confocal optical system has a radius on the order of magnitude close to the Airy disk diameter of the beam spot of the image signal light 82 at this position in order to secure the resolution of the images. That is to say, when expression (4) is applied, the radius r is minute. With regard to the radius of the aperture of the pinhole plate 51 on the side of the wavefront sensor 2, since it is necessary to allow the wavefront detection light 81 even with an aberration to pass through the aperture, the radius is sufficiently larger than the Airy disk diameter of the spot of the wavefront detection light 81. Therefore, as long as expression (4) is satisfied with respect to the pinhole plate 51, the diffracted light does not pass through the pinhole plate 52.

As described above, in a configuration in which light of the same wavelength is used as both the light for wavefront detection and the light for obtaining images, and the light is irradiated onto an examination target via a reflective liquid crystal SLM serving as a wavefront corrector, it is possible to eliminate diffracted light from the reflective liquid crystal SLM and to perform favorable wavefront detection and obtain an image with high light-use efficiency. This eliminates the necessity for a light source and a optical system for wavefront detection and enables the entire optical system to be kept compact and the cost to be reduced. Even in the case where a deformable mirror of a type having a large number of periodically arranged micromirrors is used as the wavefront corrector, the same effects can be achieved by applying the above-described configuration.

In particular, in the case where a liquid crystal SLM is used as the wavefront corrector, in order to use light of a different wavelength as the light for wavefront detection, direct this light into the eye to be examined without involving the liquid crystal SLM, and branch a wavefront detection optical path, a method that uses a dichroic mirror that reflects light in a wavelength-selective manner is also conceivable. This method enables the wavefront detector to be prevented from being irradiated with diffracted light of the light for obtaining images, which has a different wavelength, diffracted from the liquid crystal SLM.

However, in this case, since the characteristics of the liquid crystal SLM include the dependence on the wavelength, even if the wavefront aberrations are corrected with respect to the wavelength of the light for wavefront detection, there still are aberrations with respect to the wavelength of the light for obtaining images. Therefore, wavefront aberration correction control cannot be simultaneously performed with respect to the light of both wavelengths, and accordingly it is not possible to perform control so as to continue correction of the wavefront aberrations at any time by simultaneously performing wavefront detection when obtaining an image. Thus, in such a case, it is necessary to irradiate the light for wavefront detection first to perform wavefront detection and wavefront aberration correction control with the light of this wavelength, operate the liquid crystal SLM with a correction instruction value (fixed value) to which a coefficient of the ratio of the wavelengths is applied, and switch the light to the light of the wavelength for obtaining images to obtain an image. In this case, it is not possible to perform recorrection of wavefront aberrations during obtaining of an image, and so if the eye moves or the state of the tear film changes, wavefront aberration correction may not be appropriately performed, and the image quality may be decreased.

On the other hand, with the configuration of this embodiment, since the light for wavefront detection is the light of the same wavelength as the light for obtaining images, the problem as described above does not arise, and wavefront detection and wavefront aberration correction can be performed in response to any change in the state of the eye even during obtaining of an image. Accordingly, the wavefront aberration correction operation is stably performed, and it is possible to stably obtain a high-quality image.

Meanwhile, there also is a method in which other light of a different wavelength from that of the light for obtaining images is used as the light for wavefront detection in order to avoid irradiation of the wavefront detector with diffracted light. The light for obtaining images is incident on the eye via the SLM, while the light for wavefront detection is incident from a position that is closer to the eye than the SLM is. Furthermore, if, instead of the beam splitter, a wavelength branching member such as a dichroic mirror is used as a member for branching into the optical path to the detector for obtaining images and the optical path to the wavefront detector, it is possible to prevent the wavefront detector from being irradiated with unwanted light resulting from the light for obtaining images being diffracted and returned from the SLM.

However, with this configuration, in the case where a liquid crystal type SLM is used as the wavefront corrector, it is not possible to continue performing correction while measuring the wavefront at any time even during obtaining of an image. The reason for this is that due to the dependence of the output characteristics of a liquid crystal on the wavelength, different correction instruction values should be sent to the SLM for different wavelengths. In a state in which wavefront correction is performed with respect to the wavelength of the light for wavefront detection, there are aberrations with respect to the light for obtaining images. That is to say, minimization of the aberrations with respect to both wavelengths cannot be simultaneously satisfied, and therefore it is necessary to perform a complicated procedure as described below in the case where light of a different wavelength is used as the wavefront detection light.

First, a wavefront is detected with the light for wavefront detection, and feedback control is performed with the SLM to correct aberrations. Then, a correction instruction value at this time is multiplied by a coefficient corresponding to the ratio to the wavelength of the light for obtaining images, and the resulting correction instruction value is sent again to the SLM. The light is switched to the light for obtaining images with the correction control stopped in this state, and an image is obtained.

That is to say, since neither wavefront detection nor recorrection can be performed during obtaining of an image, if the state of aberrations changes due to a change in the position of the eye or a change in the state of the tear film, this cannot be dealt with, and it is difficult to stably obtain a favorable image. Moreover, for a deformable mirror consisting of a two-dimensional array of micromirrors, although the problem of the difference in wavelength between the light for obtaining images and the light for wavefront detection does not arise, another light source, an optical system for forming another optical path for the other light source, and the like are required, and this requirement results in a complicated configuration and may cause an increase in the cost.

In contrast, with the configuration of this embodiment, the above-described complicated procedure can be avoided.

As described above, according to this embodiment, the effect of diffracted light generated by the wavefront corrector on wavefront detection can be reduced by a simple configuration without performing a complicated procedure.

It should be noted that although a configuration in which light is irradiated via a liquid crystal SLM has been described in this embodiment, it is not necessarily required that the irradiation is via the liquid crystal SLM. For example, another configuration may be used in which light for aberration measurement is irradiated from near an objective lens.

In addition, although a reflective liquid crystal SLM has been given as an example in the foregoing description, the present invention is also applicable to a transmission liquid crystal SLM. Even a transmission liquid crystal SLM does not transmit the entire incident light, and a part of the incident light may be reflected by the liquid crystal surface. Thus, if the reflected light is obtained as the light for aberration correction or the light for obtaining images, there is a risk that the same problem as that of the reflective liquid crystal SLM may arise. A wide application of the present invention to SLMs, whether the reflection type or the transmission type, the effect of diffracted light generated by the wavefront corrector on wavefront detection can be reduced by a simple configuration.

It should be noted that although the shielding unit that shields diffracted light generated at the aberration correction unit has been described in the first embodiment, in addition to the diffracted light, the shielding unit may also shield a part of the returning light, for example, light contained in the returning light and unwanted in terms of aberration measurement.

In that case, the shielding unit shields a part of the returning light from the object to be examined that is irradiated with light. Then, aberrations of light, of the returning light, that has passed through the aperture of the shielding unit are detected. The aperture is configured so that the length of the aperture is shorter than the distance between the position of light shielded by the shielding unit and the position of the returning light at the shielding unit. The size of the aperture may also be changed based on the aberration detection result. For example, the size of the aperture may be changed so that the size is decreased if the amount of the detected aberrations is smaller than a threshold.

Second Embodiment

Angle of Incidence on Wavefront Corrector

Figure 4:
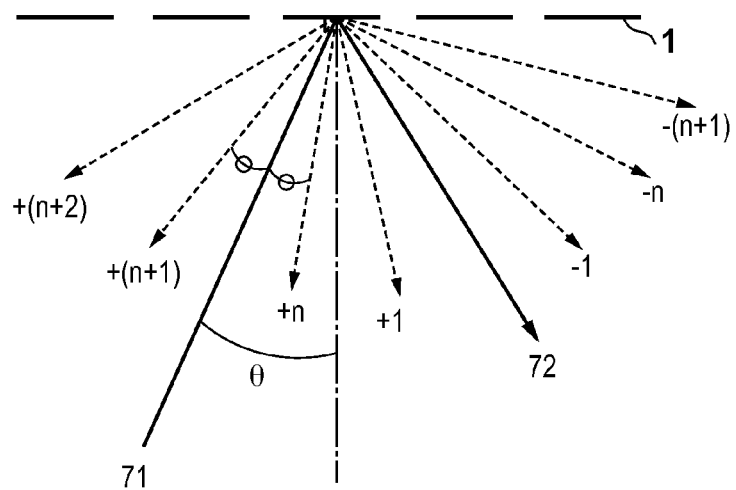
FIG. 4 is a diagram showing an example of the configuration of a part of an adaptive optical apparatus according to a second embodiment.

Referring to FIG. 4, the configuration of a part of an adaptive optical apparatus according to a second embodiment will be described. In the first embodiment, the incident angle θ of light was set so that the distance d between the position at which the diffracted light ray 91 of the order that is adjacent to the wavefront detection light 81 is irradiated onto the pinhole plate and the position at which the wavefront detection light 81 is irradiated onto the pinhole plate is larger than the radius r of the aperture of the pinhole plate. In this case, expression (4) is satisfied. At this time, if the radius r of the aperture of the pinhole plate can be made relatively small, or if the angle between diffracted light rays is relatively large because the SLM 1 has a relatively small pixel pitch, the distance between the position at which the wavefront detection light 81 is irradiated onto the pinhole plate and the position at which the diffracted light is irradiated onto the pinhole plate is relatively large. Thus, the degree of freedom of the incident angle θ at which the light is irradiated onto the SLM 1 is relatively large. On the other hand, if the radius r of the aperture of the pinhole plate 51 is relatively large, or if the angle between diffracted light rays is relatively small because the SLM 1 has a relatively large pixel pitch, the distance between the position at which the wavefront detection light 81 is irradiated onto the pinhole plate and the position at which the diffracted light is irradiated onto the pinhole plate is relatively small. Thus, the degree of freedom of the incident angle θ at which the light is irradiated onto the SLM 1 is relatively small.

The condition for this is that, as shown in FIG. 4, the light 71 is configured so as to be irradiated onto the SLM 1 from between the diffracted light of an n-th order and the diffracted light of an (n+1)-th order, which is adjacent to the n-th order. That is to say, when the diffraction angle of the n-th order is $\beta_n$, and the diffraction angle of the (n+1)-th order is $\beta_{n+1}$, it is sufficient that the incident angle θ of the light satisfies a relationship given by equation (5):

$$\theta = \beta_n + (\beta_{n+1} - \beta_n)/2 = (\beta_{n+1} + \beta_n)/2 \quad (5).$$

Therefore, $$\begin{aligned}
\sin 2\theta &= \sin(\beta_{n+1} + \beta_n) \\
&= \sin(\beta_{n+1}) \cdot \cos(\beta_n) + \cos(\beta_{n+1}) \cdot \sin(\beta_n) \\
&= \{(n+1) \cdot \lambda / P - \sin\theta\} \cdot \cos(\beta_n) + \cos(\beta_{n+1}) \cdot (n \cdot \lambda / P - \sin\theta) \\
&= \{(n+1) \cdot \lambda / P - \sin\theta\} \cdot \sin(\Pi/2 + \beta_n) + \\
&\quad \sin(\Pi/2 + \beta_{n+1}) \cdot (n \cdot \lambda / P - \sin\theta) \\
&= \{(n+1) \cdot \lambda / P - \sin\theta\} \cdot \{n \cdot \lambda / P - \sin(\Pi/2 + \theta)\} + \\
&\quad \{(n+1) \cdot \lambda / P - \sin(\Pi/2 + \theta)\} \cdot (n \cdot \lambda / P - \sin\theta) \\
&= (n+1) \cdot \lambda / P \cdot n \cdot \lambda / P - (n+1) \cdot \lambda / P \cdot \sin(\Pi/2 + \theta) - \\
&\quad \sin\theta \cdot n \cdot \lambda / P + \sin\theta \cdot \cos\theta + (n+1) \cdot \lambda / P \cdot n \cdot \lambda / P - (n+1) \cdot \\
&\quad \lambda / P \cdot \sin\theta - \sin(\Pi/2 + \theta) \cdot n \cdot \lambda / P + \cos\theta \cdot \sin\theta \\
&= 2 \cdot n \cdot (n+1) \cdot (\lambda/P)2 - (n+1) \cdot \lambda / P \cdot \sin(\Pi/2 + \theta) + \\
&\quad \sin 2\theta - (2n+1) \cdot \lambda / P \cdot \sin\theta - \sin(\Pi/2 + \theta) \cdot n \cdot \lambda / P.
\end{aligned}$$

Therefore, $2 \cdot n \cdot (n+1) \cdot (\lambda/P)2 - (n+1) \cdot \lambda/P \cdot \cos\theta - (2n+1) \cdot \lambda/P \cdot \sin\theta - \cos\theta \cdot n \cdot \lambda/P = 0$ $\Leftrightarrow 2 \cdot n \cdot (n+1) \cdot (\lambda/P)2 - (n+1) \cdot \lambda/P \cdot \cos\theta - (2n+1) \cdot \lambda/P \cdot \sin\theta - n \cdot \lambda/P \cdot \cos\theta = 0$ $\Leftrightarrow 2 \cdot n \cdot (n+1) \cdot (\lambda/P)2 - (2n+1) \cdot \lambda/P \cdot \cos\theta - (2n+1) \cdot \lambda/P \cdot \sin\theta = 0$ $\Leftrightarrow 2 \cdot n \cdot (n+1) \cdot (\lambda/P)2 - (2n+1) \cdot \lambda/P \cdot \cos\theta - (2n+1) \cdot \lambda/P \cdot \sin\theta = 0$ $\Leftrightarrow 2 \cdot n \cdot (n+1) \cdot (\lambda/P)2 - (2n+1) \cdot \lambda/P \cdot (\cos\theta + \sin\theta) = 0$.

Therefore, it is preferable to dispose the optical system so that a condition $$\cos\theta + \sin\theta = 2 \cdot n \cdot (n+1)/2(n+1) \cdot \lambda/P \quad (6)$$

is satisfied. Thus, the position at which the diffracted light is irradiated onto the pinhole plate can be spaced relatively far apart from the position at which the wavefront detection light 81 is irradiated onto the pinhole plate. As a result of this, the effect of shielding the diffracted light can be enhanced.

Third Embodiment

Changing Unit Changing Size of Aperture Through which Returning Light Passes

Figure 5A:
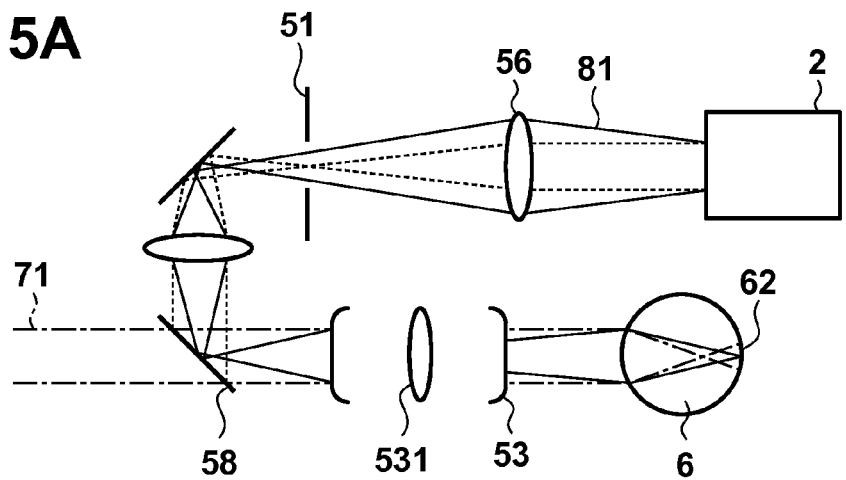
FIGS. 5A and 5B are diagrams showing an example of the configuration of a part of an adaptive optical apparatus according to a third embodiment.
Figure 5B:
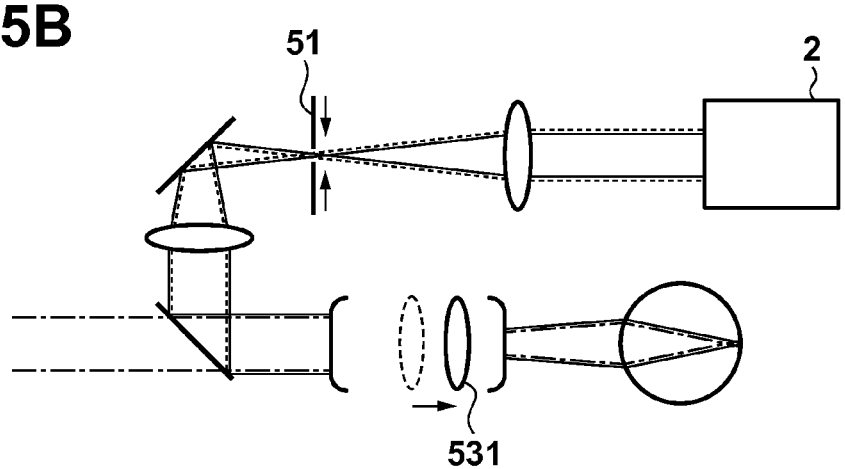

Referring to FIGS. 5A and 5B, an example of the configuration of a part of an adaptive optical apparatus according to a third embodiment will be described. Here, the SLM, the deflector, the light source, the light detector, and the like are omitted. In the first and second embodiments, the size of the aperture of the pinhole plate 51 was fixed at a size that enables shielding of the diffracted light from the SLM. In this embodiment, the pinhole plate 51 is configured by a mechanism (an example of a changing unit) that changes the size of the aperture. Thus, a configuration can be achieved in which unwanted reflected light from the cornea and an element of the optical system, such as a lens, is prevented from falling on the wavefront sensor 2 as far as possible.

Here, in order to enhance the effect of eliminating the unwanted light, the radius of the aperture of the pinhole plate 51 should be as small as possible. However, in a state in which aberrations are not corrected, if the radius of the aperture of the pinhole plate 51 is too small, even the returning light from the retina 62, which originally is to be detected, is blocked, and aberration detection cannot be correctly performed any more. For example, as shown in FIG. 5A, if the eye to be examined 6 is myopic, the retina 62 and the pinhole plate 51 are not optically conjugate, and thus an intermediate image forming point is shifted toward the eye to be examined 6 rather than at the pinhole plate 51. This results in a blur and therefore an increased spot size at the pinhole plate 51.

Here, the mechanism (an example of the changing unit) that changes the size of the aperture of the pinhole plate 51 is provided. The computer 10, which is an example of the control unit, controls the changing unit in such a manner that at the start of the initial wavefront detection, the radius r of the aperture of the pinhole plate 51 is increased so that the returning light from the retina 62 is not blocked. However, if the size of the aperture is excessively increased, the diffracted light from the SLM passes through the pinhole plate 51 and is irradiated onto the wavefront sensor 2. Thus, it is necessary that the radius r of the aperture should be adjusted to a value (e.g., $r_0$) that satisfies expression (4).

In this state, aberrations of the wavefront detection light 81 are detected by the wavefront sensor 2, and a defocus component thereof is calculated. In accordance with this defocus component, an adjustment is made by moving a focus lens 531 installed in the optical system as indicated in FIG. 5B so that the amount of defocus becomes approximately zero. Since the pinhole plate 51 is provided in a position that is optically substantially conjugate to the retina, the wavefront detection light 81 is focused close to the aperture of the pinhole plate 51. It should be noted that the adjustment may also be made so that the amount of defocus becomes smaller than a threshold, or the adjustment may also be made so that the detected aberrations become smaller than a threshold.

When this state (e.g., the detected aberrations are smaller than the threshold) is achieved, the computer 10, which is an example of the control unit, adjusts the radius of the aperture of the pinhole plate 51 to a value (e.g., $r_1$) smaller than $r_0$, and based on the value of the aberrations detected by the wavefront sensor 2, the wavefront aberrations are corrected with the SLM, which is not shown. It should be noted that an astigmatic component may also be corrected using a trial lens or the like before reducing the radius of the variable aperture of the pinhole plate 51, and the pinhole diameter may also be gradually reduced in accordance with the amount of aberrations while correcting the overall aberrations including higher-order aberrations with the SLM.

Moreover, although the radius r of the aperture of the pinhole plate 51 is variable in this embodiment, the same effect can be achieved by, for example, a configuration in which any of a plurality of pinhole plates of different sizes is inserted/removed into/from the optical path.

Thus, it is possible to suppress the effect of unwanted light that is caused by various factors and perform precise wavefront detection. Consequently, favorable wavefront correction can be performed, and the image quality can be enhanced.

According to the present invention, diffracted light that is generated when the aberration corrector is irradiated with light can be shielded upstream of the wavefront detector. This enables the effect of the diffracted light on wavefront detection to be reduced.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-269787 filed on Dec. 10, 2012, which is hereby incorporated by reference herein in its entirety.

What is claimed is:

1. An adaptive optical apparatus comprising:
an aberration correction unit configured to correct an aberration of at least irradiation light for irradiating an object to be examined and returning light from the object to be examined irradiated with the irradiation light;
a shielding unit configured to shield diffracted light that is generated at the aberration correction unit that is irradiated with at least the irradiation light and the returning light;
a detection unit configured to detect an aberration of the returning light through an aperture of the shielding unit; and
a control unit configured to control the aberration correction unit based on a detection result of the detection unit.

2. The adaptive optical apparatus according to claim 1, wherein the object to be examined is an eye to be examined,
wherein the aberration correction unit is disposed in a position that is optically substantially conjugate to an anterior ocular segment of the eye to be examined, and
wherein the shielding unit is disposed in a position that is optically substantially conjugate to a retina of the eye to be examined.

3. The adaptive optical apparatus according to claim 1, wherein the aperture has a length that is shorter than a distance between a position of the diffracted light at the shielding unit and a position of the returning light at the shielding unit.

4. The adaptive optical apparatus according to claim 1, wherein a light source for generating light for obtaining an image of the object to be examined doubles as a light source for generating light for detecting the aberration.

5. The adaptive optical apparatus according to claim 1, wherein the light is configured to be irradiated onto the aberration correction unit from between adjacent rays of the diffracted light.

6. The adaptive optical apparatus according to claim 1, further comprising:
a changing unit configured to change a size of the aperture, wherein the control unit controls the changing unit based on the detection result of the detection unit under-controlling the aberration correction unit.

7. The adaptive optical apparatus according to claim 6, wherein the control unit controls the changing unit so that the size of the aperture is decreased if the amount of the detected aberration is smaller than a threshold.

8. The adaptive optical apparatus according to claim 1, wherein the aberration correction unit is a spatial light modulator that uses a liquid crystal or a deformable mirror that has a plurality of micromirrors.

9. The adaptive optical apparatus according to claim 1, wherein the aberration correction unit is a wavefront corrector that has a two-dimensional matrix structure, and
wherein a relationship $|\{\theta - \sin^{-1}(n \cdot \lambda/P - \sin\theta)\} \cdot f| > r$ is satisfied, where P is a pitch of a periodic structure of the two-dimensional matrix structure, $\lambda$ is a wavelength of the light, $\theta$ is an angle at which the light is incident on the wavefront corrector, r is a diameter of the aperture of the shielding unit through which the returning light is allowed to pass, f is a focal length of an optical system between the wavefront corrector and the shielding unit, and n is an integer.

10. An image obtaining apparatus comprising:
the adaptive optical apparatus according to claim 1;
a measurement unit configured to measure returning light that returns from the object to be examined via the adaptive optical apparatus; and
an image obtaining unit configured to obtain an image of the object to be examined based on the measured returning light.

11. The image obtaining apparatus according to claim 10, wherein the aberration correction unit corrects an aberration of the returning light from the object to be examined even while the image is being obtained by the image obtaining unit.

12. A method for controlling an adaptive optical apparatus comprising (a) an aberration correction unit configured to correct an aberration of at least irradiation light for irradiating an object to be examined and returning light from the object to be examined irradiated with the irradiation light and (b) a shielding unit configured to shield diffracted light that is generated at the aberration correction unit that is irradiated with at least the irradiation light and the returning light, the method comprising:
a detection step of detecting an aberration of the returning light through an aperture of the shielding unit; and
a control step of controlling the aberration correction unit based on a detection result of the detection step.

13. A non-transitory computer-readable storage medium storing a computer program for causing a computer to execute the steps of the method for controlling the adaptive optical apparatus according to claim 12.

14. An adaptive optical apparatus comprising:
an aberration correction unit configured to correct an aberration of at least irradiation light for irradiating an object to be examined and returning light from the object to be examined irradiated with the irradiation light;
a shielding unit configured to shield a part of the returning light via the aberration correction unit; and
a detection unit configured to detect an aberration of light through an aperture of the shielding unit in the returning light,
wherein the aperture has a length that is shorter than a distance between a position of light that is shielded by the shielding unit and a position of the returning light at the shielding unit.

15. The adaptive optical apparatus according to claim 14, wherein the object to be examined is an eye to be examined,
wherein the aberration correction unit is disposed in a position that is optically substantially conjugate to an anterior ocular segment of the eye to be examined, and
wherein the shielding unit is disposed in a position that is optically substantially conjugate to a retina of the eye to be examined.

16. An adaptive optical apparatus comprising:
an aberration correction unit configured to correct an aberration of at least irradiation light for irradiating an object to be examined and returning light from the object to be examined irradiated with the irradiation light;
a shielding unit configured to shield a part of the returning light via the aberration correction unit;
a detection unit configured to detect an aberration of light through an aperture of the shielding unit in the returning light;
a changing unit configured to change a size of the aperture; and
a control unit configured to control the changing unit based on a detection result of the detection unit under-controlling the aberration correction unit.

17. The adaptive optical apparatus according to claim 16, wherein the control unit controls the changing unit so that the size of the aperture is decreased if the amount of the detected aberration is smaller than a threshold.

18. The adaptive optical apparatus according to claim 16, wherein the object to be examined is an eye to be examined,
wherein the aberration correction unit is disposed in a position that is optically substantially conjugate to an anterior ocular segment of the eye to be examined,
wherein the shielding unit is disposed in a position that is optically substantially conjugate to a retina of the eye to be examined and shields, as the part of the returning light, a returning light from a region other than the retina.

19. A method for controlling an adaptive optical apparatus comprising (a) an aberration correction unit configured to correct an aberration of at least irradiation light for irradiating an object to be examined and returning light from the object to be examined irradiated with the irradiation light and (b) a shielding unit configured to shield a part of the returning light via the aberration correction unit, the method comprising:
a detection step of detecting an aberration of light through an aperture of the shielding unit in the returning light; and
a control step of controlling a changing unit configured to change a size of the aperture based on a detection result of the detection step under-controlling the aberration correction unit.

20. A non-transitory computer-readable storage medium storing a computer program for causing a computer to execute the steps of the method for controlling the adaptive optical apparatus according to claim 19.

* * * * *